(12) United States Patent
Matousek et al.

(10) Patent No.: US 8,159,664 B2
(45) Date of Patent: Apr. 17, 2012

(54) APPARATUS FOR DEPTH-SELECTIVE RAMAN SPECTROSCOPY

(75) Inventors: Pavel Matousek, Oxfordshire (GB); Anthony William Parker, Wiltshire (GB)

(73) Assignee: The Science and Technology Facilities Council, Oxfordshire (GB)

( * ) Notice: Subject to any disclaimer, the term of this patent is extended or adjusted under 35 U.S.C. 154(b) by 0 days.

(21) Appl. No.: 12/637,421

(22) Filed: Dec. 14, 2009

(65) Prior Publication Data

US 2010/0091276 A1    Apr. 15, 2010

Related U.S. Application Data

(63) Continuation of application No. 11/792,684, filed as application No. PCT/GB2005/004535 on Nov. 25, 2005, now Pat. No. 7,652,763.

(60) Provisional application No. 60/669,880, filed on Apr. 11, 2005.

(30) Foreign Application Priority Data

Dec. 9, 2004    (GB) .................................. 0426993.2

(51) Int. Cl.
*G01J 3/44*    (2006.01)
(52) U.S. Cl. ...................................................... 356/301
(58) Field of Classification Search .................. 356/300, 356/301, 72–73
See application file for complete search history.

(56) References Cited

U.S. PATENT DOCUMENTS

| | | | |
|---|---|---|---|
| 4,570,638 | A | 2/1986 | Stoddart et al. |
| 5,139,025 | A | 8/1992 | Lewis et al. |
| 5,194,913 | A | 3/1993 | Myrick et al. |
| 5,261,410 | A | 11/1993 | Alfano et al. |
| 5,349,961 | A | 9/1994 | Stoddart et al. |
| 5,371,368 | A | 12/1994 | Alfano et al. |
| 5,565,982 | A | 10/1996 | Lee et al. |
| 5,615,673 | A | 4/1997 | Berger et al. |
| 5,625,458 | A | 4/1997 | Alfano et al. |
| 5,660,181 | A | 8/1997 | Ho et al. |
| 5,752,519 | A | 5/1998 | Benaron et al. |
| 5,842,995 | A | 12/1998 | Mahadevan-Jansen et al. |

(Continued)

FOREIGN PATENT DOCUMENTS

EP    1 475 037 A1    11/2004

(Continued)

OTHER PUBLICATIONS

Dunsby C et al: "Techniques for depth-resolved imaging through turbid media including coherence-gated imaging" Journal of Physics D. Applied Physics, IOP Publishing, Bristol, GB, vol. 36, 2003, pp. R207-R227.

(Continued)

*Primary Examiner* — Tarifur Chowdhury
*Assistant Examiner* — Abdullahi Nur
(74) *Attorney, Agent, or Firm* — Birch, Stewart, Kolasch & Birch, LLP

(57) ABSTRACT

Apparatus and methods for detecting Raman spectral features non destructively from sub-surface regions of a diffusely scattering sample are disclosed. Incident radiation is supplied at one or more sample surface entry regions, and light is collected from one or more collection regions spaced from the entry regions. Raman features are detected in the collected light, and depth information is derived according to the entry-collection spacings.

58 Claims, 11 Drawing Sheets

U.S. PATENT DOCUMENTS

| | | | |
|---|---|---|---|
| 5,873,831 A | 2/1999 | Bernstein et al. | |
| 5,935,062 A | 8/1999 | Messerschmidt et al. | |
| 5,999,836 A | 12/1999 | Nelson et al. | |
| 6,289,230 B1 | 9/2001 | Chaiken et al. | |
| 6,310,686 B1 | 10/2001 | Jiang | |
| 6,321,111 B1 | 11/2001 | Perelman et al. | |
| 6,352,502 B1 | 3/2002 | Chaiken et al. | |
| 6,681,133 B2 | 1/2004 | Chaiken et al. | |
| 7,072,700 B2 | 7/2006 | Yamamoto et al. | |
| 2003/0004419 A1 | 1/2003 | Treado et al. | |
| 2003/0018272 A1 | 1/2003 | Treado et al. | |
| 2003/0116436 A1* | 6/2003 | Amirkhanian et al. | 204/452 |
| 2003/0220549 A1 | 11/2003 | Liu et al. | |
| 2004/0054270 A1 | 3/2004 | Pewzner et al. | |
| 2004/0133251 A1 | 7/2004 | Altshuler et al. | |
| 2004/0186383 A1 | 9/2004 | Rava et al. | |
| 2005/0010130 A1* | 1/2005 | Morris et al. | 600/562 |

FOREIGN PATENT DOCUMENTS

| | | |
|---|---|---|
| JP | 56-22938 A | 3/1981 |
| JP | 10-500323 A | 1/1998 |
| JP | H-11-508033 A | 7/1999 |
| JP | 2001-178708 A | 7/2001 |
| JP | 2002-85385 A | 3/2002 |
| JP | 2002-512830 A | 5/2002 |
| JP | 2003-010189 | 1/2003 |
| JP | 2004-248849 | 9/2004 |
| JP | 2004-294150 A | 10/2004 |
| WO | WO-92/15008 A1 | 9/1992 |
| WO | WO 95/26676 A1 | 10/1995 |
| WO | WO-96/26431 A1 | 8/1996 |
| WO | WO 96/29925 A2 | 10/1996 |
| WO | WO-98/00057 A1 | 1/1998 |
| WO | WO 99/55222 A1 | 11/1999 |
| WO | WO-00/16036 A1 | 3/2000 |
| WO | WO-00/20843 A1 | 4/2000 |
| WO | WO-01/39665 A3 | 6/2001 |
| WO | WO-01/52739 A1 | 7/2001 |
| WO | WO-02/07585 A2 | 1/2002 |
| WO | WO-03/023382 A | 3/2003 |
| WO | WO-03/041123 A3 | 5/2003 |
| WO | WO 03/068070 A1 | 8/2003 |
| WO | WO-03/073082 A1 | 9/2003 |
| WO | WO-03/087793 A1 | 10/2003 |
| WO | WO 2004/051242 A1 | 6/2004 |
| WO | WO-2004/078044 A1 | 9/2004 |
| WO | WO-2004/078045 A1 | 9/2004 |
| WO | WO-2004/097365 A2 | 11/2004 |
| WO | WO-2005/004714 A1 | 1/2005 |
| WO | WO-2006/061565 A1 | 6/2006 |
| WO | WO-2007/040589 A1 | 4/2007 |

OTHER PUBLICATIONS

Matousek P "Fluorescence background suppression in Raman spectroscopy using combined Kerr gated and shifted excitation Raman difference techniques" Journal of Raman Spectroscopy vol. 33, No. 4, Apr. 2002, pp. 238-242.

Matousek et al., Applied Spectroscopy, vol. 59, No. 4, 2005, pp. 393-400.

Butterfield, "Through-package applications of Raman spectroscopy for non-desstructive identification of product," Nov. 1999, p. 14 (XP-002450781).

Haka et al., Cancer Research, vol. 62, Sep. 15, 2002, pp. 5375-5380.

Kincade et al.,"Optical diagnostics image tissues and tumors", Laser Focus World, Feb. 1996, pp. 1-5.

Hasegawa, Trends in Analytical Chemistry, vol. 20, No. 2, 2001, pp. 53-64.

Wu et al., Applied Optics, vol. 34, No. 18, Jun. 20, 1995, pp. 3425-3430.

Ma et al., Applied Spectroscopy, vol. 51, No. 12, 1997, pp. 1845-1848.

Matousek., Journal of Raman Spectroscopy, vol. 32, 2001. pp. 983-988.

2007 No. 770 Scientific Research—The Research Councils (Transfer of Property etc) Order 2007.

J. Klosowski and E. Steger, "Experiments on Raman Versus Primary Light Scattering Fluxes From Pressed Discs", Journal of Raman Spectroscopy. vol. 8, No. 3, 1979, pp. 169-171.

B. Schrader and G. Bergmann, "Intensity of the Raman Spectrum of Polycrystalline Substances", Fresenius Journal of Analytical Chemistry, vol. 225, 1967, pp. 230-247.

* cited by examiner

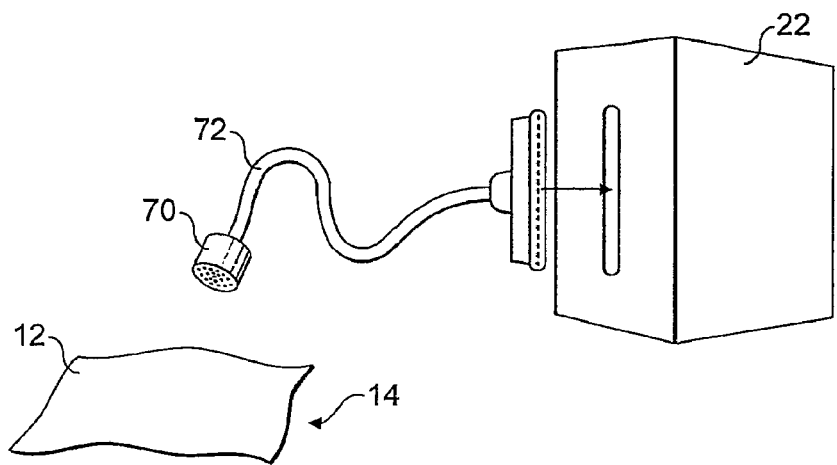
FIG. 6
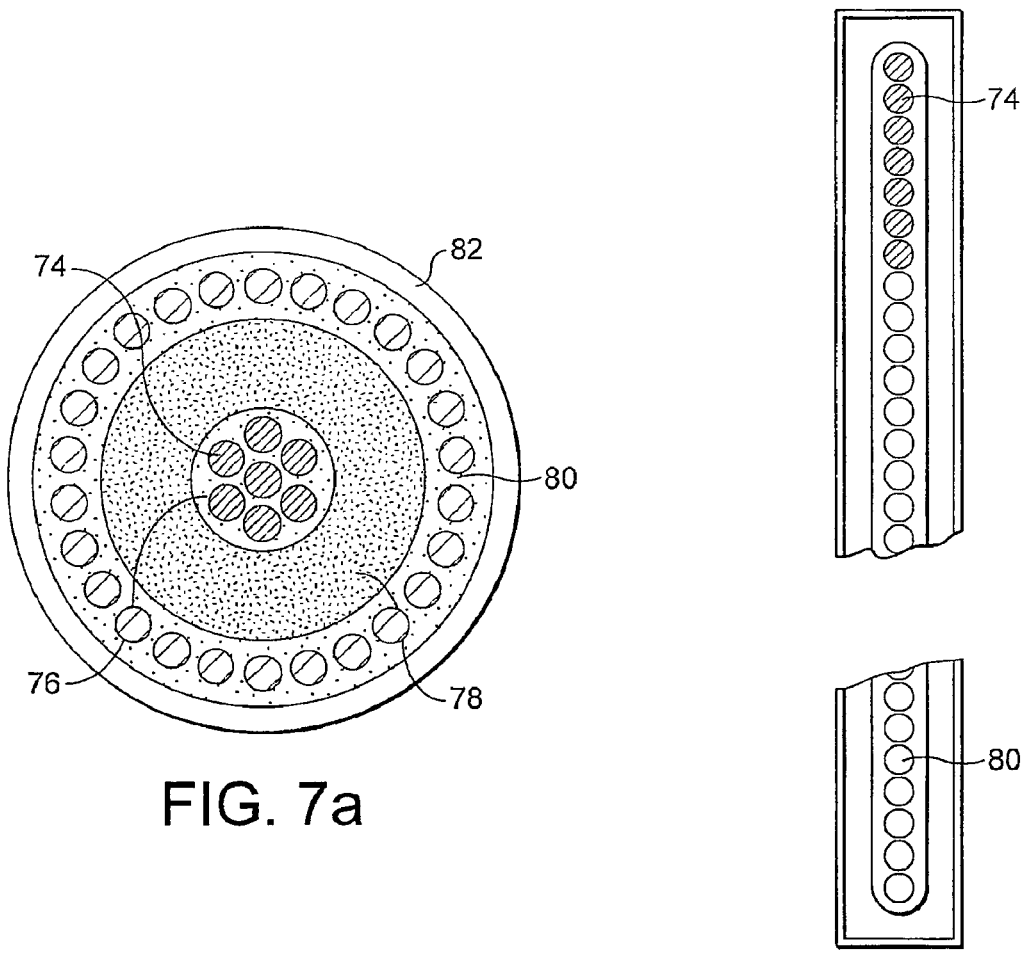
FIG. 7a
FIG. 7b

APPARATUS FOR DEPTH-SELECTIVE RAMAN SPECTROSCOPY

This application is a Continuation of co-pending application Ser. No. 11/792,684 filed on Jun. 8, 2007, which is a National Phase of PCT/GB2005/004535 filed Nov. 25, 2005 for which priority is claimed under 35 U.S.C. §120 and also claims priority under 35 U.S.C. 119(e) to U.S. Provisional Application No. 60/669,880 filed on Apr. 11, 2005; and this application claims priority of Application No. 0426993.2 filed in United Kingdom on Dec. 9, 2004 under 35 U.S.C. §119; the entire contents of all are hereby incorporated by reference.

FIELD OF THE INVENTION

This invention relates to the field of Raman spectroscopy and, in particular, to apparatus for detecting Raman spectral features non-destructively from sub-surface regions within a macroscopic diffusely scattering sample.

Diffusely scattering media are frequently encountered in many analytical applications. Examples of such analytical applications include but are not limited to monitoring of food products, colloids, polymers, catalysts, powders in general, coating technology and medical applications involving the probing of tissue and biochemical identification in medical studies and treatments. The samples encountered in such analytical applications are often highly heterogeneous and can be made of various layers each having a different chemical make-up. Therefore, a major goal for analytical science is to provide a method capable of determining the chemical composition of sub-surface layers in a non-destructive way.

The benefits that can be derived from the analysis of chemical compositions can be illustrated using the example of non-invasive Raman probing of bones where signal quality from bone can be crucial in arriving at an accurate and correct diagnosis as to whether disease is present (see A. Carden and M. D. Morris, J. Biomed. Optics 5, 259 (2000)). Conventional Raman signatures of bone collagen are masked by undesired Raman signals from overlaying tissue and so data on chemical composition is generally obtained by means of a biopsy.

The separation of Raman spectral components derived from a surface layer of a sample and from a sub-surface layer of the same sample would be highly desirable in many analytical applications. This task is, however, hugely complicated due to an inability to form sharp optical images from within turbid media of the overlying material by conventional optical methods such as confocal microscopy, which is only applicable typically to depths of the order of the transport length of the scattering medium (the transport length describes the average distance photons travel before deviating significantly from their original direction of propagation). This length is typically around ten times the mean free scattering path of photons in the medium. For example, in biological tissue this corresponds to depths of around several hundred micrometres.

DESCRIPTION OF THE PRIOR ART

Infrared and Raman spectroscopies are known to provide a wealth of information on the physio-chemical state of a wide range of biological tissues and fluids (see, for example U.S. Pat. No. 6,681,133 or WO 01/52739). Unfortunately analysis by these methods has largely been limited to surface studies.

Elastically scattered photons have been used to probe beneath a scattering surface for compositional information. For example, B. B. Das, et al. in Rep. Prog. Phys. 60, 227 (1997) describes an approach using temporal gating. This technique relies on the fact that it takes a finite time for light to penetrate a diffusely scattering medium. Scattering events will therefore occur later at lower depths, and so monitoring a scattered signal over time should, theoretically, provide information as to the nature of the scattering centres at progressively greater depths. The elastic scattering technique of Das et al. is, however, not directly applicable to Raman spectroscopy. Inelastic scattering of photons has a far smaller cross-section, resulting in a much weaker signal. Furthermore the Raman signal is far more susceptible to interference from luminescence and in particular fluorescence when analysing tissue.

SUMMARY OF THE INVENTION

It is an object of this invention, therefore, to provide an analysis technique based on Raman spectroscopy that is capable of extracting sub-surface chemical compositional information.

Accordingly the invention provides a method of measuring sub-surface Raman scattering through a diffusely scattering sample or medium, to thereby determine characteristics of the sub-surface region. In one aspect the method comprises: (a) supplying incident radiation at an entry region on a surface of the sample, for example using a light probe supplied by a laser; (b) collecting, from a collection region on the surface, light scattered within the sample, the collection region being spaced from the entry region; and (c) detecting, in the collected light, one or more Raman features spectrally related to the incident radiation.

Just a single spacing between the entry and collection regions may be required to obtain information about a sub-surface layer if sufficient prior knowledge is available, such as intensities of expected Raman features of the near surface region of the sample. However, by determining Raman spectral intensities at a variety of spacings more accurate information can be derived, for example using techniques described in more detail below.

A reference collection region may also be provided at substantially the same place or overlapping with the entry region, for comparison with a spaced collection region. Advantageously, such a colocated reference collection region may share common optics with the light source supplying the incident radiation.

A variety of collection region and entry region geometries are possible. In one preferred embodiment the collection region forms an annulus around the entry region. Multiple such annular collection regions, or a single variable radius region may be used to derive more depth related data, and the arrangement may be reversed by placing a single fixed or variable or multiple annular entry region around a central collection region. It should be noted that the annular regions may be broken or incomplete and will generally not include full optical coverage within these regions. For example, a circular single thickness array of closely packed optical fibres might attain a 60% coverage.

A collection region is preferably spaced at least 1 mm and more preferably at least 2 mm from an associated entry region. The depth of a sub-surface layer to be studied will typically be similar to this spacing distance, and the practical dimensions will depend on the optical properties of the sample. The diameter or size of the entry region will generally be less than the spacing of the entry and collection regions, and the entry and collection regions are preferably non-overlapping.

The present invention also provides a method of measuring a sub-surface Raman spectrum of a diffusely-scattering sample, the method comprising the steps of:

a) irradiating an entry region of the sample with a light probe;
b) collecting light scattered by the sample; and
c) spectrally separating at least a portion of the collected light to detect one or more Raman spectral features, wherein light scattered by the sample is collected from a plurality of spatial locations or collection regions on the surface of the sample, each spatial location being at a different distance from the point of irradiation, at least a portion of the light collected at each spatial location being separately spectrally dispersed to form a plurality of Raman spectra and wherein the method further includes the step of:

d) analysing the plurality of Raman spectra to extract information on the Raman spectrum of a sub-surface region of the sample.

Thus, spectroscopic information is obtained non destructively that can be interpreted to establish the nature and composition of a diffusely scattering sample below a surface layer. The present invention as defined by the methods outlined above effectively implements a form of spatial gating of the Raman signal obtained from the sample to isolate the Raman signal from a sub-surface layer which has a different composition to that of the surface layer. This method is referred to herein as Spatially Offset Raman Spectroscopy (SORS).

With the present invention for samples having one or more different chemical compositions at differing depths within the sample, the collection of Raman spectra from regions spatially offset, by different amounts, from the point of incidence of the probe laser beam results in a series of spectra (two or more spectra) each spectra including Raman signals emanating from different depths within the sample. The series of spectra taken contain different relative contributions of the Raman signals generated from the sample surface layer and the sample sub-surface layers. In collecting the data series, as the signal collection point is moved away from the point of incidence of the probe laser beam, the contribution of the surface layer signal diminishes much faster than for signals generated by different compositions at deeper layers within the bulk of the sample. This enables the contribution of deeper, sub-surface layers to be extracted either directly or by applying numerical processing to the collected spectral set for a higher degree of separation (e.g. multivariate data analysis or scaled subtraction of spectra from each other).

In a preferred embodiment two or more Raman spectra are collected and are analysed using a scaled subtraction, the Raman spectrum collected from or at a distance closest to the point of irradiation being subtracted from the Raman spectrum collected further from the point of irradiation, whereby features of the Raman spectrum for a sub-layer of the sample are identified.

In a further alternative, where the Raman spectrum for the chemical composition of the surface of the sample is known, the collected Raman spectra are analysed by scaled subtraction of the known Raman spectrum from the Raman spectra of the collected light.

In an alternative preferred embodiment at least twenty Raman spectra are collected at different distances from the point of irradiation and the plurality of Raman spectra are analysed-using multivariate data analysis. Principal component analysis may be used as the multivariate data analysis.

A preferred feature of the present invention is irradiation of the sample at two or more different wavelengths, where the collected light is a combination of a Raman spectrum and fluorescence, so that the Raman spectrum can be extracted from the collected light.

At least one of the sample, the collection optics and the point of irradiation may be moved relative to the others to enable the collection of Raman spectra at different distances from the point of irradiation. A movable stage may be provided on which the sample is mounted and the probe beam is arranged to track the movement of the sample whereby the sample is moved relative to fixed collection optics for the collection of scattered light at different distances from the point of irradiation.

The scattered light may be collected from point regions at different distances from the point of irradiation or the scattered light may be collected from a plurality of substantially parallel lines substantially transverse to the distance as measured from the point of irradiation.

Alternatively, the probe beam may be supplied using optical fibres and the scattered light may be collected using optical fibres arranged in a plurality of concentric circles around the probe beam optical fibres whereby the scattered light is collected in concentric rings at differing radii from the point of irradiation.

Ideally, the light probe is at >200 nm and <2000 nm and may be generated by one or more quasi-monochromatic lasers or a diode laser which is tunable, for example with respect to temperature.

In an alternative aspect the present invention provides apparatus for selectively measuring Raman spectra generated at different depths within a diffusely-scattering medium, the apparatus comprising: a light source for irradiating a sample with a probe beam; collection optics for collecting light scattered by the sample and passing it to a spectrometer; detection means for detecting light dispersed by the spectrometer, wherein the apparatus is adapted for scattered light to be collected at a plurality of spatial locations on the surface of the sample, each spatial location being at a different distance from the point of irradiation and at least a portion of the light collected at each spatial location being separately spectrally dispersed by the spectrometer to form a plurality of Raman spectra and wherein the apparatus further includes an analyser for identifying features specific to the Raman spectrum of a sub-layer of the sample from the plurality of Raman spectra.

The apparatus preferably includes a movable stage for relative movement of at least one of the sample, the collection optics and the point of irradiation to enable the collection of Raman spectra at different distances from the point of irradiation. Alternatively, the collection optics may comprise optical fibres arranged in a plurality of concentric circles around the probe beam.

The light source may consist of one or more quasi-monochromatic lasers or a diode laser which are tunable, for example with respect to temperature.

In a further alternative aspect the present invention provides a method of diagnosis comprising collecting from a sample, consisting of a surface region of an overlying tissue and a sub-layer region of a deep tissue which is different to the overlying tissue, one or more Raman spectra using the method as described above.

Preferably one or more features specific to the Raman spectrum of the sub-layer region of the sample are identified in the one or more collected Raman spectra and are compared with those obtained from a healthy control specimen.

Embodiments of the invention will now be described by way of example only and with reference to the accompanying drawings.

BRIEF DESCRIPTION OF THE DRAWINGS

FIG. 6 shows an optical head 70 for coupling to a spectral detector 22;

FIGS. 7a and 7b show plan details of the optical head and connector of FIG. 6;

DETAILED DESCRIPTION OF THE PREFERRED EMBODIMENTS

Figure 1:
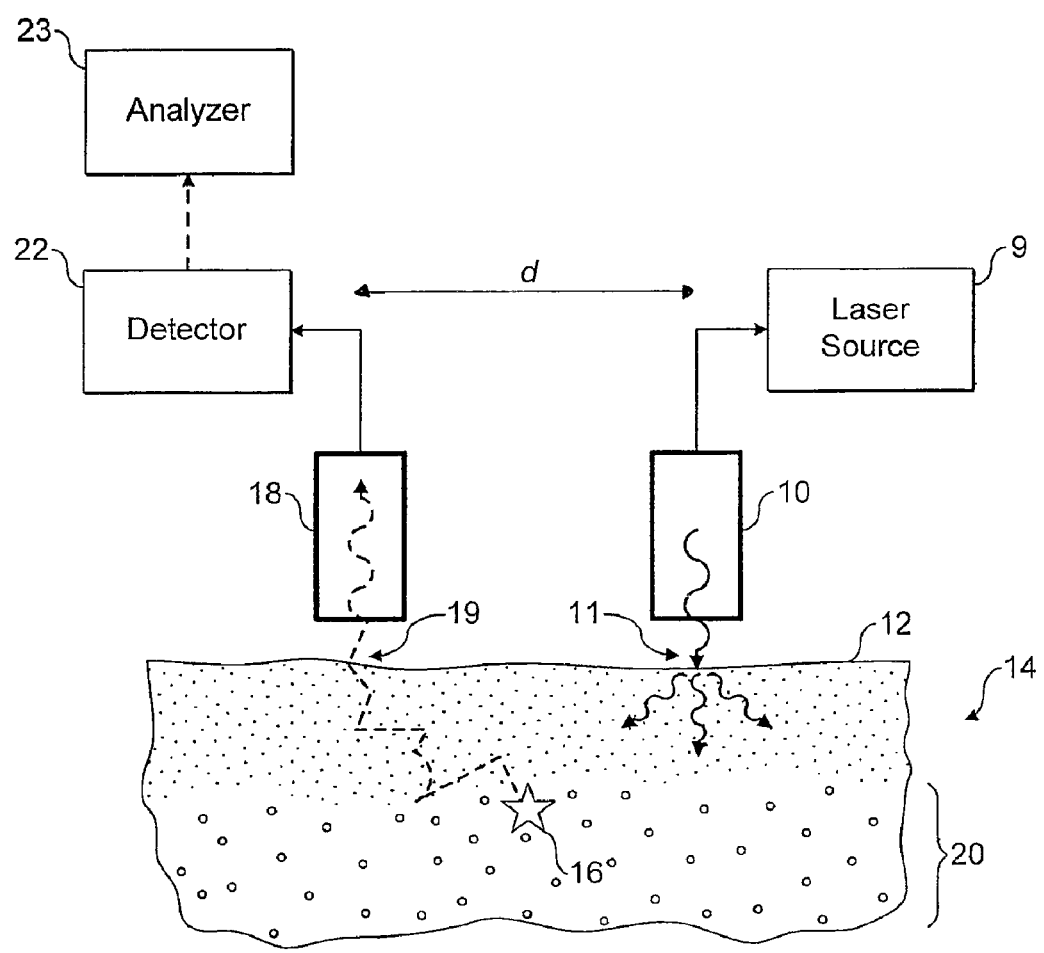
FIG. 1 illustrates principles of the invention, in which illumination by source 10 leads to a Raman scattering 16 in a sub-surface region of sample 14, the Raman photon being received at collector 18.

Referring now to FIG. 1 an embodiment of the invention is shown in operation, in schematic cross section. A light source 10, incorporating or supplied by laser 9, is used to irradiate a localised entry region 11 of a surface 12 of a sample 14. The incident radiation from the light source is scattered diffusely through the sample. Some of the radiation may be absorbed by the sample, some may give rise to optical emissions for example by fluorescence, and some re-emerges unchanged through the sample surface 12.

A small proportion of the photons of the incident radiation are inelastically scattered giving rise to Raman photons, for example as illustrated by Raman event 16. The Raman photons in turn are diffusively scattered through the sample. Some may be absorbed, for example giving rise to fluorescence, but some emerge unchanged through the surface 12 to be collected at collector 18. The likelihood of a Raman photon undergoing a second Raman event is very small.

The collected light is analysed, for example using filters or a spectrometer, and a suitable sensor in detector 22, and the determined Raman spectra or spectral features are used further in analyzer 23, which is typically a computer. The detector may use a fourier transform rather than a conventional dispersive spectroscopic technique.

Typically, most Raman photons will be generated close to the light source 10, where the incident radiation is most intense. These Raman photons can best be detected by collecting light at the light source 10, for example by using optics common with the light source. As distance from the light source increases, however, the intensity of Raman photons originating near the light source falls away more quickly than the intensity of Raman photons originating further away from the light source, especially from deeper within the sample. Preferential sampling of Raman photons from deeper within the sample can therefore be achieved by spacing the location at which light is collected from the location at which the sample is illuminated, and an analysis of how the detected spectral features change with spacing can provide more detailed sub-surface information.

In FIG. 1 Raman event 16 occurs in a subsurface layer 20. The spacing d between the light source 10 and the collector 18, or equivalently between an entry region 11 and a collection region 19 can be adjusted to select for a particular depth. In preferred embodiments, however, light is collected at a range of two or more spacings d, and an analyzer 23 is used to infer depth dependent characteristics of the sample from the Raman features of the collected and analyzed light for different values of d, which are spectrally analyzed by analyzer 22. One of the spacings could be at, or very close to the entry region.

For example, the analyzer may preferentially select (or reject) the Raman features for a particular depth or range of depths by combining the Raman features for different spacings. Some techniques for this, including scaled subtraction and PCA are discussed below.

Figure 2A:
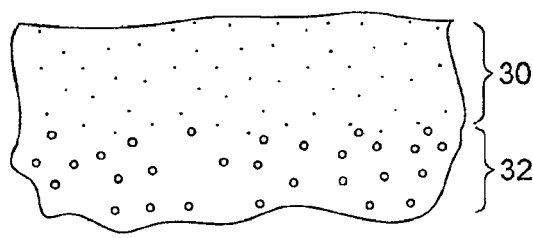
FIGS. 2a to 2c illustrate various sample layer arrangements.
Figure 2B:
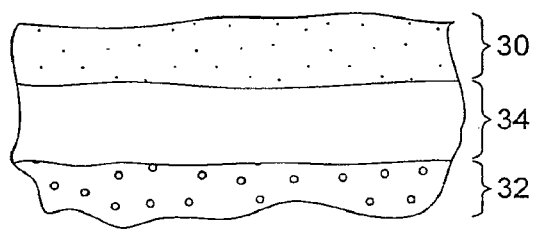
Figure 2C:
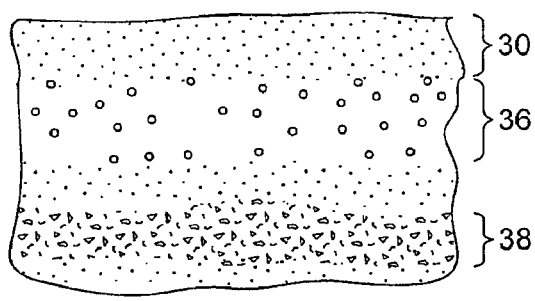

In FIG. 1 the sample 14 displays a non-abrupt boundary between the surface region and sublayer 20. In FIGS. 2a to 2c some other sample configurations are shown. In FIG. 2a there is an abrupt change from surface layer 30 to deep layer 32, and deep layer 32 may be diffusely scattering, or partly or completely opaque, with Raman photons representative of layer 32 being generated at the layer interface. In FIG. 2b the surface layer 30 and the deep layer 32 are separated by a further transparent or semi transparent layer 34 which may be, for example, a space filled with a liquid or gas. In FIG. 2c a more complex sample is shown, in which graduated or abrupt sublayers 36 and 38 are embedded beneath or within the surface layer 30.

Figure 3A:
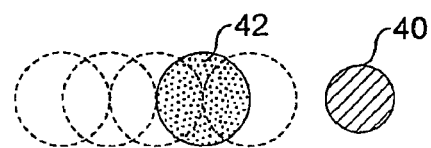
FIGS. 3a to 3c illustrate various entry and collection region arrangements.

The incident irradiation and collection of light at a single, at multiple or at a variable spacing can be achieved using a variety of geometries. In FIG. 3a there is a single illumination or entry region 40 on the sample surface. Spaced from this illumination region is either a single collection point or region 42, or multiple regions as indicated by the broken lines. Alternatively the single collection region, or equivalently the illumination region may be moved to provide a variable spacing.

Figure 3B:
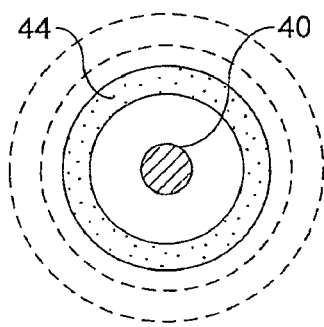

In FIG. 3b the single illumination region 40 is surrounded by an annular collection region 44, or by multiple or a variable radius annular collection region as indicated by the broken lines. Instead of an annular collection region, a broken annulus or multiple separate regions at similar distances from the point of illumination could be used.

Figure 3C:
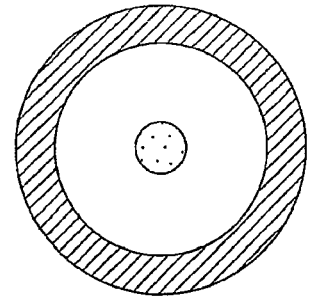

In FIG. 3c an annular illumination region 46 and central collection region 48 are used, thereby reducing the localised intensity of incident radiation required to generate a given number of Raman photons. The annulus may be varied in radius or be provided as multiple annuli having a range of radii, and a broken annulus of multiple separate illumination regions distributed at similar distances from the central point of collection may be used.

Generally, it is beneficial to collect light, or to provide incident radiation at as large a proportion of an entry or collection region as possible. However, in practical embodiments the coverage may be limited. For example, in arranging cylindrical optical fibres in an annulus a coverage of 10% or more may be adequate, but 25% or more would be preferred and 60% or more may be possible.

In simplistic embodiments a single entry region may be provided by a single optical fibre brought close to the sample surface, and multiple collection regions may be provided by a linear array of collection fibres. Optical fibres may be similarly used to provide annular and other configurations of single and multiple fixed spacings and various mechanical arrangements may be used to provide variable spacings.

Figure 4:
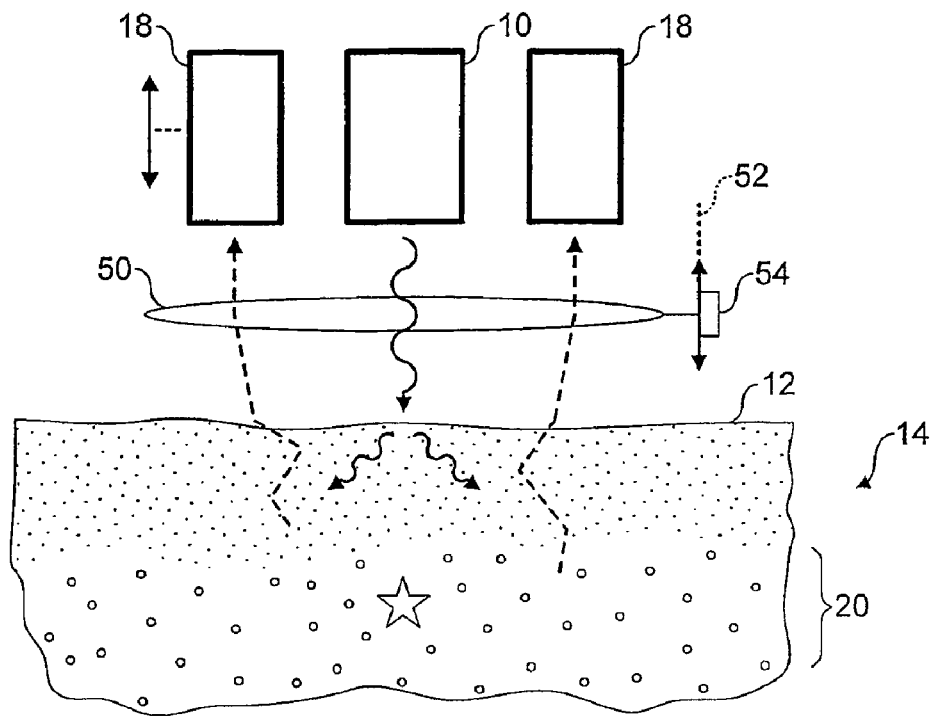
FIG. 4 shows an arrangement for varying the diameter of an annular collection region using an optical arrangement 50, 54.

To provide a variable radius entry region or collection region an optical arrangement such as that illustrated in FIG. 4 may also be used. Optics 50 located between the sample and the collector and/or sample-to-detector distance is adjustable to direct light from different parts of the sample surface onto collector 18 which is concentric with the light source 10. In this arrangement, a lens arrangement (and/or the illumination source and Raman collector detector position) which can be translated in an axial direction 52 by an optics drive 54 directs light from an annular region of varying radius onto the collector, but other configurations are also envisaged.

Figure 5:
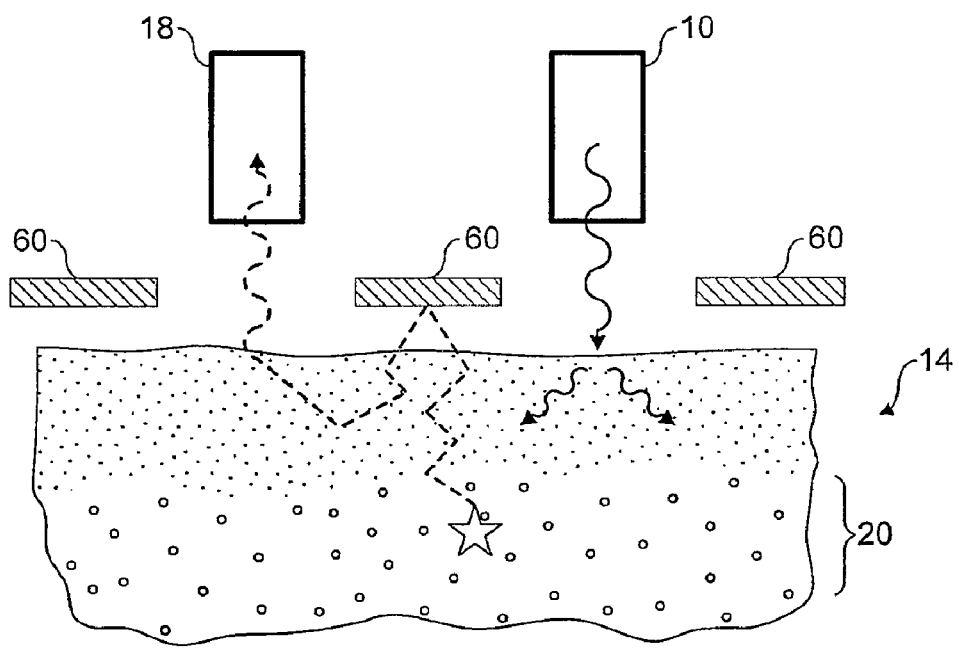
FIG. 5 illustrates the use of mirrors 60 to enhance the collection of Raman photons.

A further aspect, which may be used with any of the arrangements discussed above, is illustrated in FIG. 5. One or more mirror elements 60 are presented to the sample surface. When either incident or Raman radiation emerges from the sample away from the collector 18, these mirror elements redirect the emerging radiation back into the sample. This increases the intensity of incident radiation and so the generation of Raman photons within the sample, and also increases the proportion of Raman photons received at the collector 18. The mirror elements are preferably absent from the surface adjacent to the light source 10 or entry region, and adjacent to the collection regions.

In alternative embodiments non-imaging optics, such as those described in Applied Optics vol 35 p 758, may be used to achieve higher collection efficiency by use of a mask placed directly onto the sample, or placed in an image plane if other imaging optics are also used. The mask blocks appropriate areas of the sample to collect signal from a desired spatial offset only. The masking is preferably synchronised with a detector such as a charge coupled device such that sequential readings from the detector relate to masks providing light collected from correspondingly sequential spacings between the illumination and collection regions. The masking could be mechanical and could also be performed between imaging optics and a non-imaging type detector.

FIG. 6 illustrates a practical embodiment of the invention comprising an optical head 70 coupled by an optical fibre bundle 72 to analyser 22. Detail of the optical head 70 is shown in the plan schematic view of FIG. 7a which is not to scale. A bundle of light source optical fibres 74 terminate in the central region of the head. These light source fibres are embedded in a filler 76 such as epoxy, and surrounded by an annular spacer element 78. Collection optical fibres 80 terminate an annular region surrounding the spacer element, again embedded in a filler, and surrounded by an external casing. This arrangement may be adapted to included the various mirror and optical arrangements discussed above.

In this particular embodiment each optical fibre has a core of 200 µm diameter and a cladding bringing the fibre thickness to 230 µm. The inner bundle consists of seven light source optical fibres 74, and the outer bundle consists of 26 collection optical fibres 80. The spacer 78 is sized to space the collection fibres 80 about 3 mm from the centre of the head, and the terminations of the collection fibres are distributed approximately evenly in an annulus of constant radius about this centre. The collection fibres should be suitable for carrying out near infra red Raman work, and may be made of silica.

The illumination and collection optical fibres terminate, about 100 cm distant from the optical head, in a connector illustrated schematically in FIG. 7b. The connector presents the six illumination and twenty six collection fibres for coupling into the analyzer 22 of FIG. 6, which incorporates a light source illumination quasi-monochromatic laser operating at 827 nm and a Kaiser Holospec optical analyser.

Figure 8:
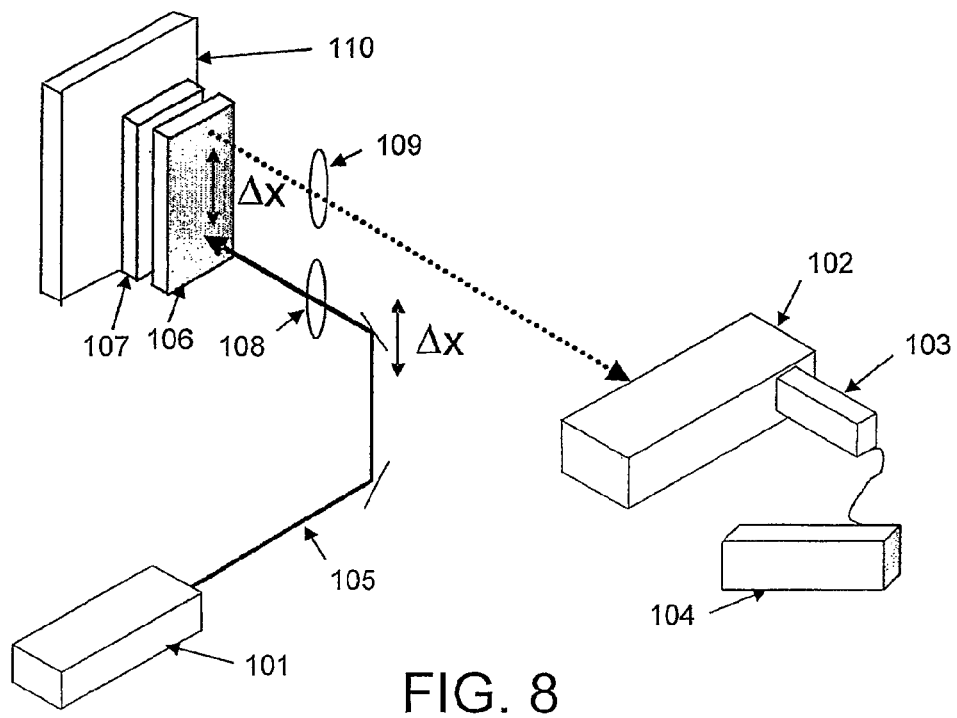
FIG. 8 illustrates schematically analysis apparatus in accordance with the present invention set up to extract Raman spectra generated beneath a surface layer of a sample.

A schematic diagram of another spatial gating analysis apparatus for identifying depth specific Raman spectra is shown in FIG. 8. The features and variations already described above may be applied here as appropriate, such as the various collection geometries, and vice versa. The apparatus generally comprises a laser 101, Raman detection apparatus 102, 103 and an analyser 104. The probe beam 105 of the apparatus is generated using a quasi-monochromatic laser such as a single-line cw argon ion laser operating at 514 nm, (in the case of tissue analysis 827 nm would be preferred to avoid fluorescence background), with 12 mW power which is directed using conventional optics at a sample. The sample has a surface layer 106 and a deeper layer 107 of a different chemical composition to that of the surface layer, and may be mounted on a stage. With this apparatus the laser plasma lines were blocked using a Pellin-Broca prism (not illustrated). The apparatus includes a 1 m focal length lens 108 for weakly focusing the laser beam onto the sample to a spot diameter of 300 µm and at normal incidence. Raman light produced as a result of the irradiation of the sample is collected in backscattering geometry using a 2" diameter collection lens 109 with f-number ~1 and is imaged with the lens 109 onto the slit of a spectrometer 102, which is part of the Raman detection apparatus, with a magnification of 2.5. A conventional imaging spectrometer 102 (for example a Spex Triplemate™ with f-number 6.3) is preferably used to disperse the Raman light and image the Raman light onto a CCD camera 103. The camera 103 is preferably a liquid nitrogen cooled back-illuminated deep depletion CCD camera (for example Andor, DU420-BU2 (250 nm) 1024×255 active pixels). The CCD quantum-efficiency of such a camera in the region of Raman spectra is around 65% and has a pixel size of 26×26 µm. The final stage slit width of the 25 spectrometer 102 was set to 120 µm. The CCD was binned vertically across 20 pixels to maintain the spatial selectivity on the collection side.

Figure 9:
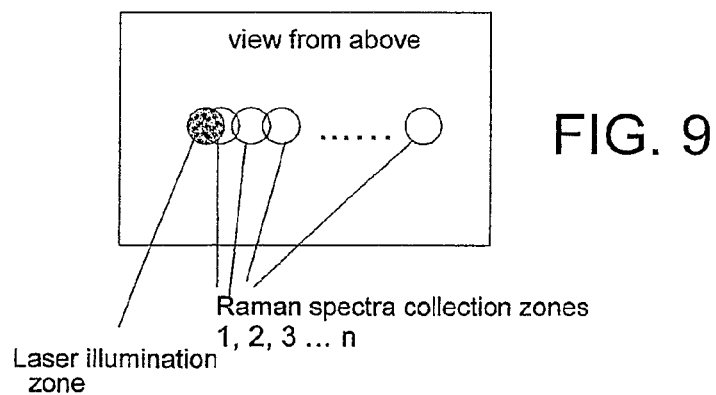
FIG. 9 illustrates a point collection geometry for collection of spatially offset Raman spectra in accordance with the present invention.

The sample 106, 107 was mounted on an x-y-z micropositioning stage 110 which includes a controlled drive (not illustrated) which moves the stage (vertically in FIG. 8) together with the final optics to keep the incidence point of the laser beam fixed on the sample with respect to the sample. In this configuration, the Raman detection apparatus 102, 103 always collects back scattered Raman shifted photons from a fixed imaging zone in space and the sample is scanned across this imaging zone whilst the pump beam incidence point remains fixed in its position on the surface of the sample. A filter (not illustrated) may also be used to block any residual elastically scattered probe laser light from reaching the spectrometer 102. The SORS apparatus described above may be deployed using a point collection laterally offset from the point of probe beam incidence (FIG. 9). Alternatively, a movable stage or other movement control means may be used for achieving relative movement between one or more of the sample, point of irradiation and the Raman detection apparatus.

Raman spectra using apparatus similar to that described above were collected for a test sample in which the first layer 106 consisted of a 1 mm optical path cuvette of 1 cm width and ~4 cm height, with 300 µm custom made fused silica front and back windows, filled with PMMA (poly(methyl methacrylate)) spheres of ~20 µm diameter. The spheres were loosely packed in the cell using mechanical tapping on the cell during filling to eliminate any larger voids. This first layer was followed by a second layer 107 consisting of another cell of 2 mm optical path filled with trans-stilbene fine powder ground using a mortar and pestle. The cuvettes were employed in order to provide a simple method of sample handling and are not an essential feature of the apparatus.

Figure 10:
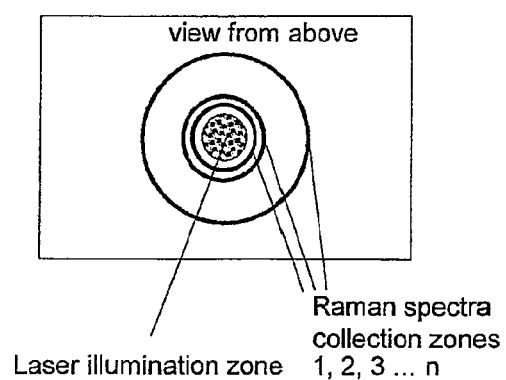
FIG. 10 illustrates a concentric circle collection geometry for collection of spatially offset Raman spectra in accordance with the present invention.

With the probe laser beam incident on the sample positioned with the first layer 106 uppermost, spatially offset Raman spectra using the SORS method described herein were collected using a basic point collection geometry in which collection is from the points laterally displaced from the probe beam's incidence point (FIG. 9). The point of collection geometry as illustrated in FIG. 9 represents the simplest implementation of the method of the present invention. On the other hand, the concentric circle geometry illustrated in FIG. 10, which does not require the use of an x-y positioning stage, advantageously yields much higher collection efficiency but involves the use of optical fibres to image the individual circles at different heights on the spectrometer slit enabling their imaging after dispersion on the CCD 103 onto separate horizontal strips with the vertical position of the spectra on the CCD corresponding to a given offset collection distance on the sample surface with respect to the probe beam's incidence point. The use of a fiber optic bundle for the collection of Raman spectra is described in an article by Jiaying Ma and Dor Ben-Amotz entitled "Rapid Micro-Raman Imaging using Fiber-Bundle Image Compression" Applied Spectroscopy Vol. 51, No. 12, 1997 the contents of which is incorporated herein by reference.

It will, of course, be apparent that further alternative collection geometries could be employed whilst still achieving spatially offset Raman spectra collection in accordance with the present invention.

Additionally, with no sample illumination, an "above the sample" Raman spectrum may be collected which represents background and apparatus noise. This "above the sample" Raman spectrum can then be subtracted from the set of Raman spectra to remove noise from the spectra.

When taking Raman spectra using the resonance Raman technique, whereby the wavelength of the incident probe beam is tuned to match chromophores of the material or materials being investigated, the Raman signatures may be swamped by fluorescence (luminescence) generated from electronic excitation. For example, fluorescence will be stimulated in room temperature studies of bone, but phosphorescence is more likely in colder samples. Similarly, Raman probing of metallic systems will often stimulate room temperature phosphorescence.

In such cases the Raman spectra can be recovered using the SORS method at two or more laser wavelengths. This relies upon the fact that the spectral profile of a fluorescent background is not normally dependent on the excitation wavelength whereas the Raman spectrum is dependent on the excitation wavelength. Hence, spectra collected at the same spatial distance from the point of illumination at two or more different wavelengths of irradiation may be subtracted from each other to give a derivative type plot of where the Raman bands are and this can be mathematically processed to give a truer looking Raman spectrum. This technique for identifying Raman bands is described in an article by S. E. J. Bell, E. S. O. Bourguignon and A. C. Dennis entitled "Subtracted shifted Raman spectroscopy (SSRS) method" Analyst, 1998, 123, 1729-1734. This technique is also referred to as the Shifted Excitation Raman Difference technique (SERD) as described in a paper of the same name by P. Matousek, M. Towrie and A. W. Parker I J. Raman Spec., 33, 128-242 (2002) the contents of which is incorporated herein by reference.

The two or more wavelengths of incident irradiation may be generated by means of separate lasers or by means of a single laser, such as a diode laser, the output of which is varied for example through temperature tuning. The difference in wavelength required is generally about half the width of the Raman bands, typically approximately 5-10 $cm^{-1}$.

Figure 11:
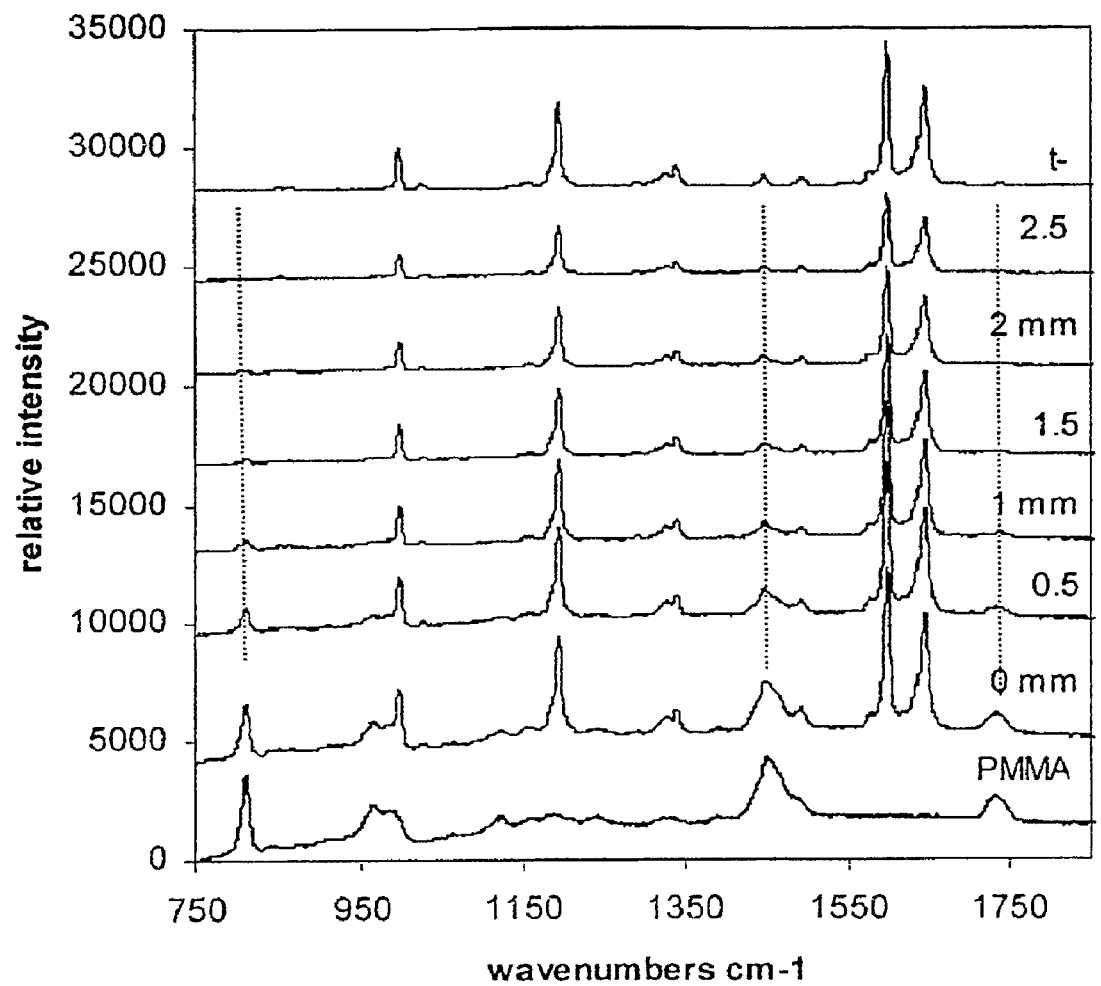
FIG. 11 shows a series of Raman spectra for a two layer sample generated at different offsets using the analysis apparatus of the present invention.

A set of Raman spectra for the test sample described above, measured with a varying degree of spatial offset with respect to the Raman collection point and the point of laser incidence on sample surface is shown in FIG. 11. For comparison, the Raman spectra of pure layers measured in separate measurements are also displayed. The top spectrum in FIG. 11 is that of pure trans-stilbene and the bottom spectra that of pure PMMA. The spectrum measured with the zero offset (0 mm) represents the Raman spectrum one would typically obtain using a conventional Raman instrument. It is evident that it contains an appreciable contribution from both the top and bottom layers of the sample and that the contribution of the top layer gradually decreases with offset distance in the spatially offset spectra. For real applications, where a pure spectrum of the bottom layer needs to be recovered, the top layer signal might represent an unacceptable distortion to the Raman signal of a lower layer. The gradual separation between the two signals is clearly accomplished using the SORS approach as the lateral offset between the Raman collection point and the point of probe beam incidence is increased and is clearly observable from the illustrated data set. At a distance of >2 mm (third spectra down in FIG. 11) an order of magnitude improvement in the ratio of the lower over the top layers Raman signals is achieved.

Figure 12:
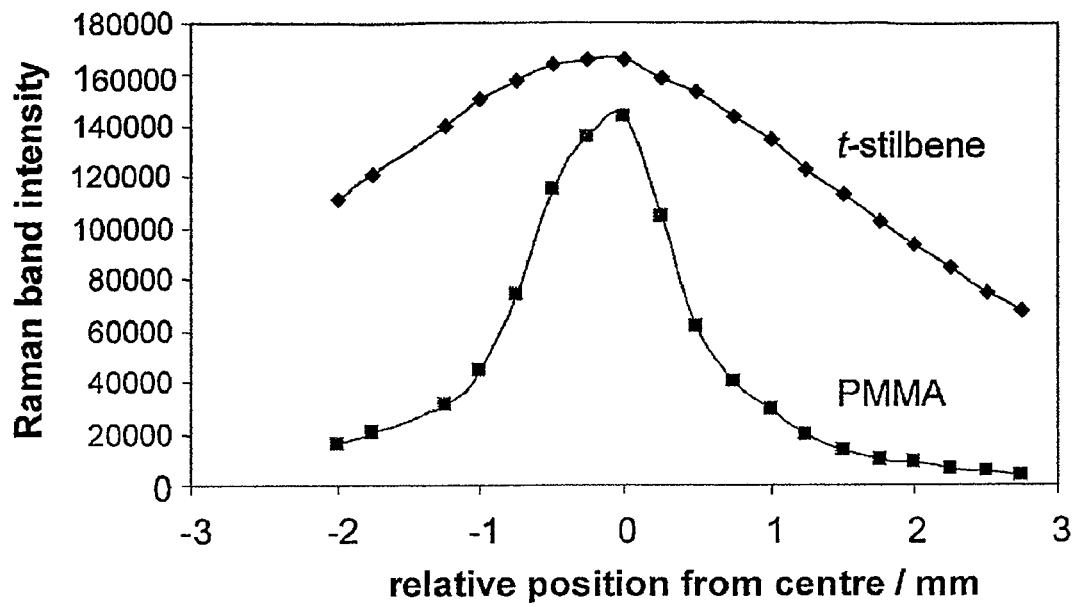
FIG. 12 illustrates the dependence on offset distance of the absolute intensities of the Raman spectra for the sample of FIG. 11.
Figure 13:
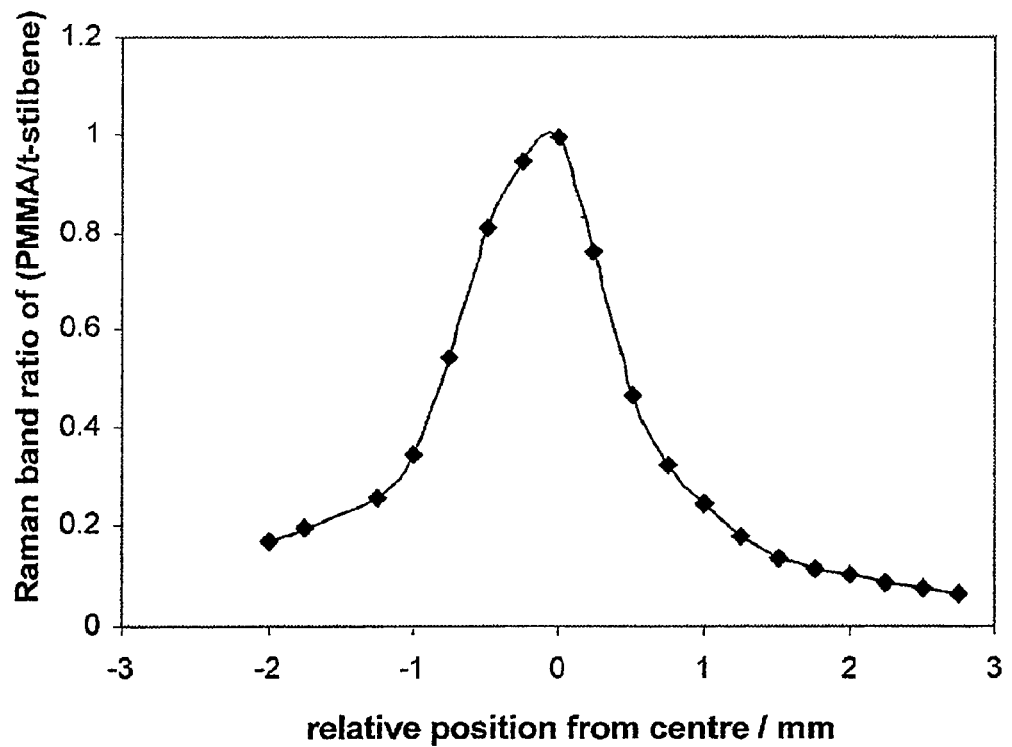
FIG. 13 illustrates the ratio of the Raman spectra of FIG. 12 with respect to offset distance.

FIG. 12 shows the dependence of the absolute Raman intensities of the individual spectra on the spatial offset. The data was obtained by numerical fitting of two intense trans-stilbene bands at 1575, 1595, 1632 and 1641 $cm^{-1}$ and bands at around 809, 1455, and 1728 $cm^{-1}$ for PMMA. The plot clearly demonstrate that as the Raman collection point is moved sideways from the probe illumination zone, i.e. the lateral offset is increased, the Raman signal from the bottom layer diminishes much more slowly than that from the top layer. This results in the overall relative Raman intensity ratio of the bottom over the top layer improving with increasing spatial offset as shown in FIG. 13.

Figure 14:
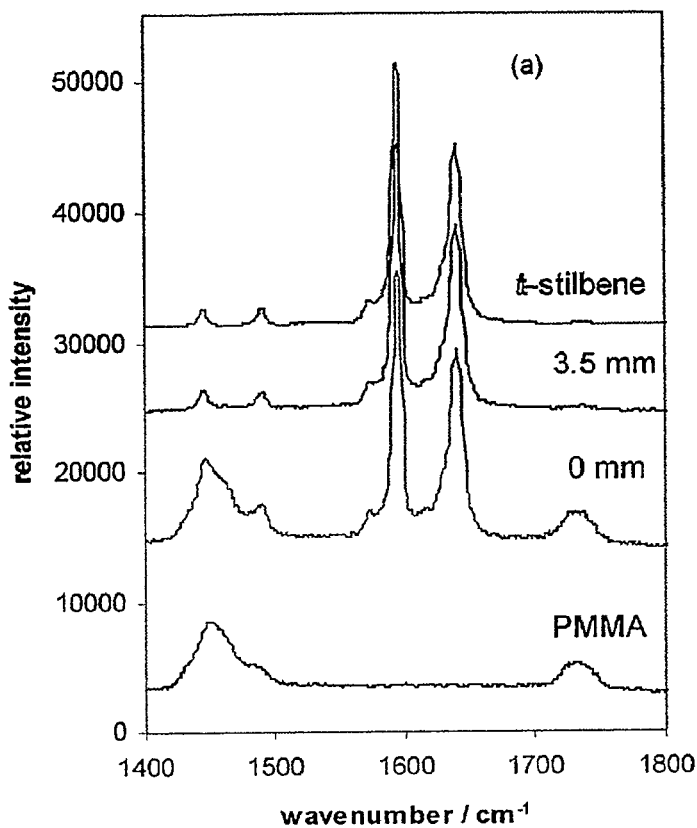
FIG. 14 shows a series of Raman spectra for the same two layer sample scaled to the same height of trans-stilbene bands.
Figure 15:
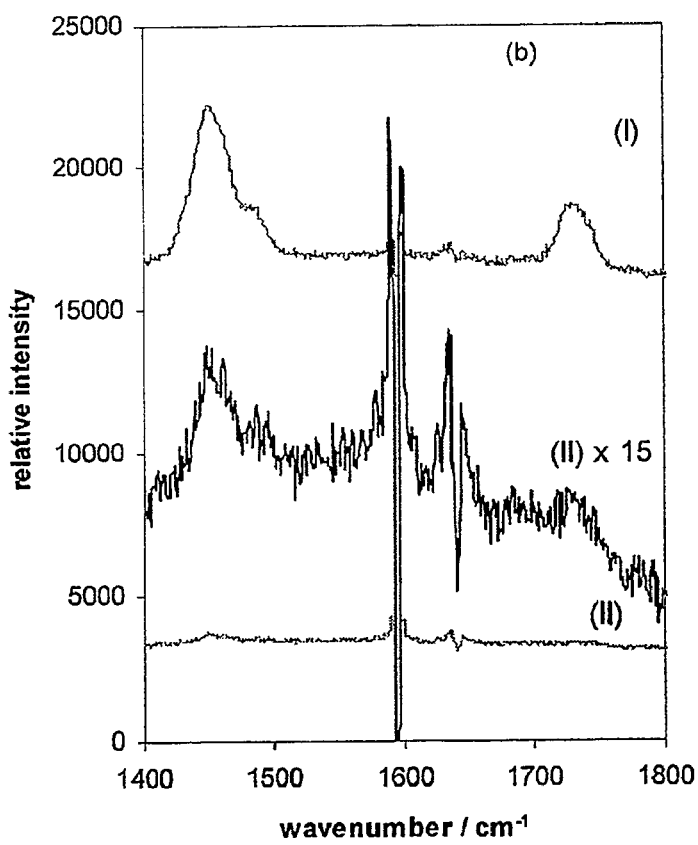
FIG. 15 illustrates the PMMA contributions within the individual spectra of FIG. 14.

To quantify the contrast improvement achieved using the method and apparatus of the present invention with respect to the test sample described above, a Raman spectrum with a longer-acquisition time (1000 s) at an offset of 3.5 mm was acquired. FIG. 14 shows this spectrum along with a Raman spectrum acquired with zero offset scaled to the same height of trans-stilbene bands. By subtracting the pure trans-stilbene spectrum from these spectra we obtained the PMMA contributions within the individual spectra (see FIG. 15). By fitting these we established that the contrast of the lower layer had been improved by a factor of 15 by rejecting the top layer spectral component. Another striking observation is that the signal-to-noise obtained using this spatial gating approach is good in comparison to alternative approaches.

The total attenuation of the Raman trans-stilbene signal by, the 1 mm PMMA layer was measured with the zero offset to be around 80. This loss of signal through the diffusion process, inevitably present also in conventional Raman spectroscopy, can be, however, effectively offset through further refinements in the collection efficiency: for example by adopting the circular collection geometry shown in FIG. 10, or by using a lower f-number and a higher throughput spectrograph.

Figure 16:
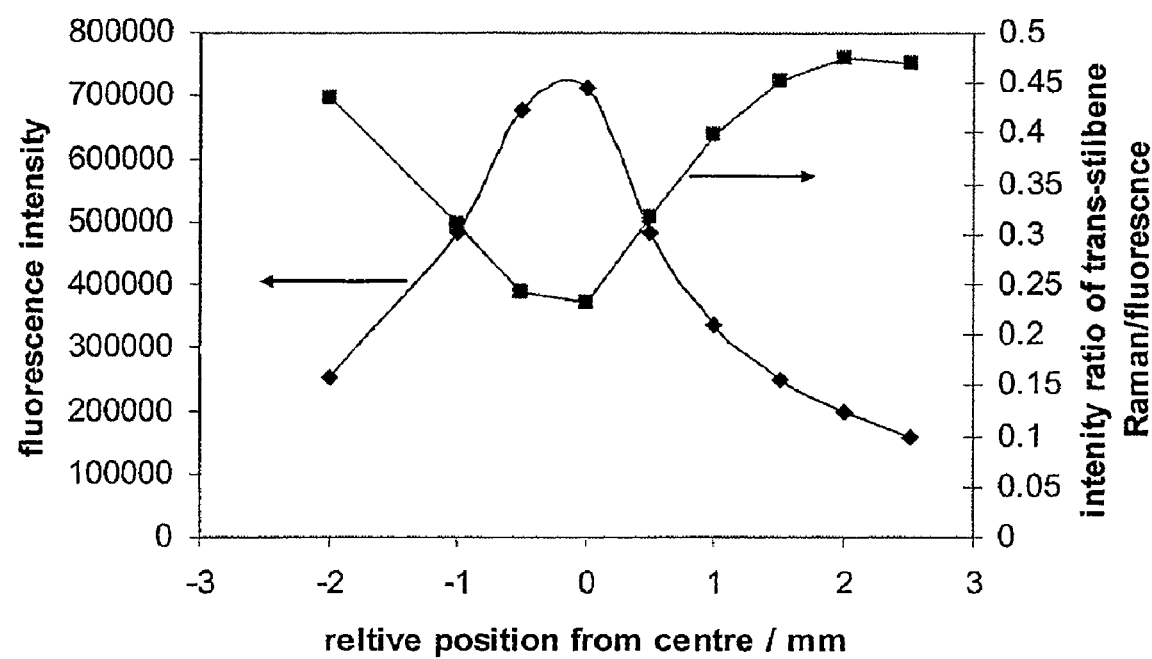
FIG. 16 shows, for the same sample, the relative ratio of a trans-stilbene Raman signal in comparison with fluorescence originating from the PMMA layer as a function of the spatial collection offset.

FIG. 16 demonstrates another useful feature of the spatial gating analysis apparatus and method of the present invention. The analysis apparatus is capable of suppressing fluorescence in the lower layer Raman spectrum if it originates from the top layer. The plot shown in FIG. 16 gives the relative ratio of the trans-stilbene Raman signal in comparison with the fluorescence originating from the PMMA layer as well as the fluorescence absolute intensity as a function of the spatial collection offset. The trans-stilbene Raman intensity relative to fluorescence intensity is improved by a factor of approx. 2 with the introduction of a 2.5 mm displacement.

In a situation where a larger separation of the data obtained from surface and sub-surface layers is required than that achievable directly within the raw spectra, by offsetting the collection and probe launch points a multivariate data analysis procedure may be deployed using the analyser 104 of FIG. 8. The data collected by SORS is particularly amenable to multivariate data analysis because for this approach to be applicable, the set of Raman spectra measured at various offsets is still required. To achieve an effective numerical decomposition the number of spectra within the set should ideally be at least an order of magnitude higher than the number of layers present in the sample. To demonstrate this a multivariate analysis of the form of principal component analysis (PCA) was employed.

Approximately twenty Raman spectra acquired on the PMMA and trans-stilbene two-layer system represented in FIG. 8 and produced using the SORS method and apparatus described herein were imported into Matlab™ R11 (The Mathworks Inc., Natick, Mass.) and processed with both built in and locally written scripts. The ten largest eigenvectors generated after performing a singular value decomposition on the original data set were included in the PCA rotation. The pure spectra of PMMA and trans-stilbene were not included in this dataset and no baseline correction was performed.

Multivariate data reduction techniques are advantageous when a complete separation of the spectral features of the surface and sub-surface layers is required. These data reduction techniques also provide a means of separating spectral features from layers that may have a moderate to high degree of spectral overlap or where contributions of individual components to spectral bands envelopes may not be known because spectra of the pure components may not be obtainable or known.

Figure 17:
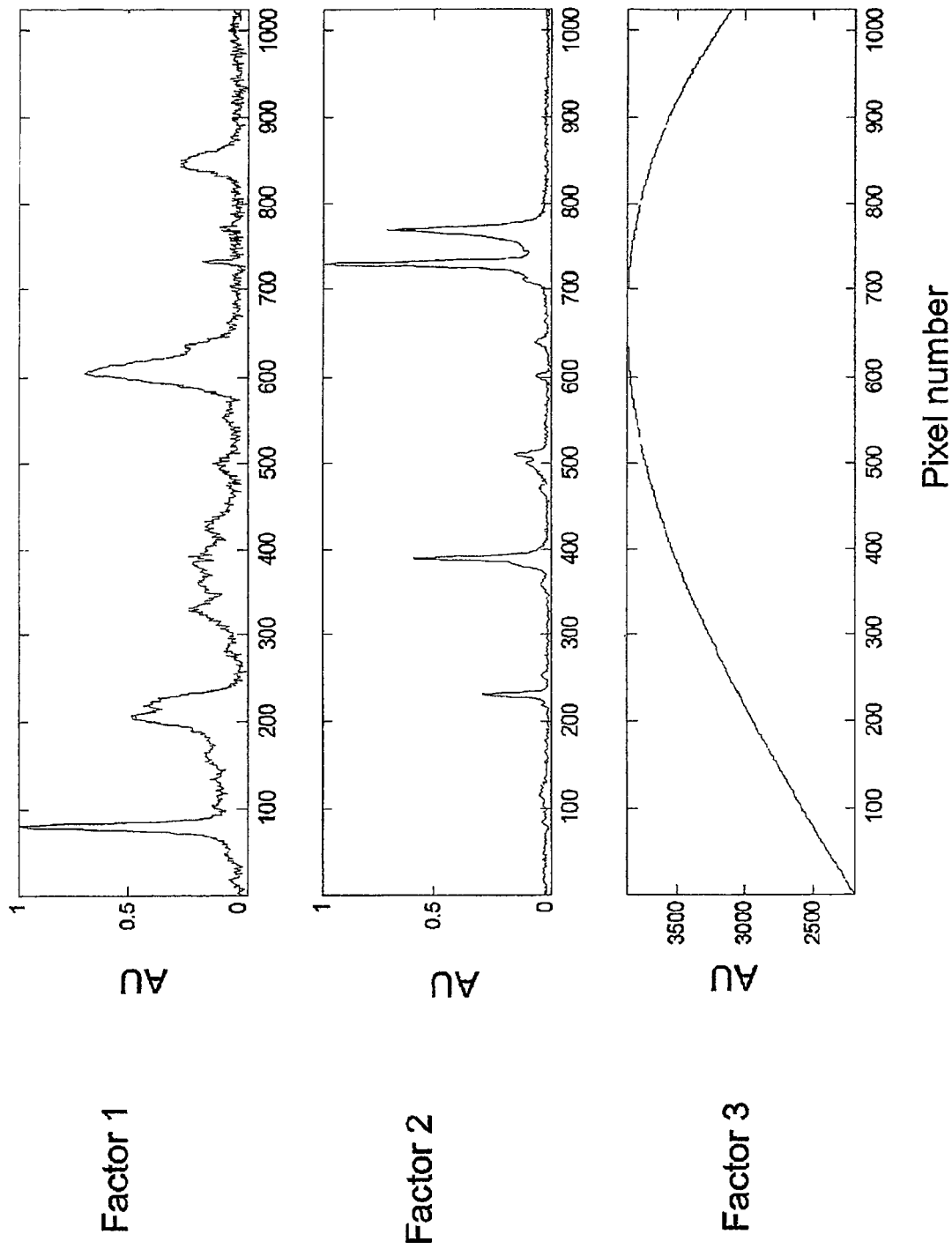
FIG. 17 shows the results of a PCA analysis of a series of Raman spectra for the same sample obtained using the analysis apparatus in accordance with the present invention.

The recovered factors from the multivariate analysis are shown in FIG. 17. The procedure cleanly decomposed the Raman spectra collected in this way into the pure spectra of the two individual layers, i.e. a PMMA (top layer) and a trans-stilbene (bottom layer). A factor for pure trans-stilbene was recovered by targeting the ca. 1595 cm$^{-1}$ band (pixel 730) and a factor for pure PMMA was recovered by targeting the ca. 809 cm$^{-1}$ band (pixel 80). The luminescence background factor was constructed from one of the original input spectra. This factor was generated using an iterative polynomial fitting algorithm (Lieber CA and Mahadevan-Jansen A 2003) typically used for baseline correction. In this case 100 fitting cycles using a third order polynomial were used to generate the baseline. This baseline was used as a factor representing the luminescence background. These three factors were then used to reconstruct the dataset with less than 3% error.

Although in the above example twenty separate Raman spectra were collected, where a scaled subtraction of individual Raman spectra is possible, as few as two or three spectra are required. Even with multivariate data analysis, although it is preferred to perform the analysis on at least a factor more than the number of components to be identified, such analysis can often be successfully performed using smaller data sets of, for example, around ten spectra.

The following is the inventors' current theory for explaining the efficacy of the analysis method and apparatus described herein. This theory is supported by detailed Monte Carlo scattering modelling studies also carried out by the inventors, which yield results in very good agreement with experiment. The variation in the relative content of Raman signals from different layers as the collection point is spatial offset originates from the random properties of the photon migration effect. The migrating photons in essence undergo a 'random walk' within the medium and the photon direction is randomised every transport length along the propagation distance. When a Raman signal is collected from the surface of a sample at the point where the probe beam is incident, the spectrum contains a relatively large signal contribution from the top layer due to the probe photon density being highest at the point of sample exposure. With increasing sample depth the probe intensity fast diminishes as the photon intensity is progressively diluted through the photon diffusion process. Moreover, Raman light generated at deeper layers of the sample is scattered as it propagates back to the surface and is subject to the same diffusion. This therefore leads to further dilution of the intensity of Raman spectra generated at deeper sample layers. This effect results in a substantially larger proportion of Raman photons generated at the sample surface being collected than those generated at deeper sample layers when a signal is collected from the surface of a sample at the point where the probe beam is incident, in comparison to the signal that would be collected for an optically transparent media probed in the same geometry.

However, when Raman light is collected from a point laterally offset from the point of probe beam incidence, the probe light intensity within the sample is becoming more equally distributed along its depth. This is because the incident light first had to propagate sideways through the sample from the probe incidence point to the collection area and was on its way randomised through photon diffusion. Consequently, the scattered Raman signal collected at a position offset from the probe incident point contains a higher proportion of the deeper layer signal than that in the spectrum collected from the probe beam incidence point.

The described spatial gating analysis apparatus and method thus offers an extremely powerful, yet simple means for extracting pure Raman signals from individual layers within diffusely scattering media. The probed sample depths can be well in excess of the transport length, which sets a depth limit on the conventional confocal Raman microscopy. In the above example, the transport length of the medium was estimated to be 200 µm. Importantly, the apparatus and method can be used 'blind', i.e. without any prior knowledge of the chemical constituents of individual layers. The technique has thus ideal prerequisites for sensitive sub-surface, non-destructive probing of diffusely scattering materials in both industrial and medical applications.

Figure 18:
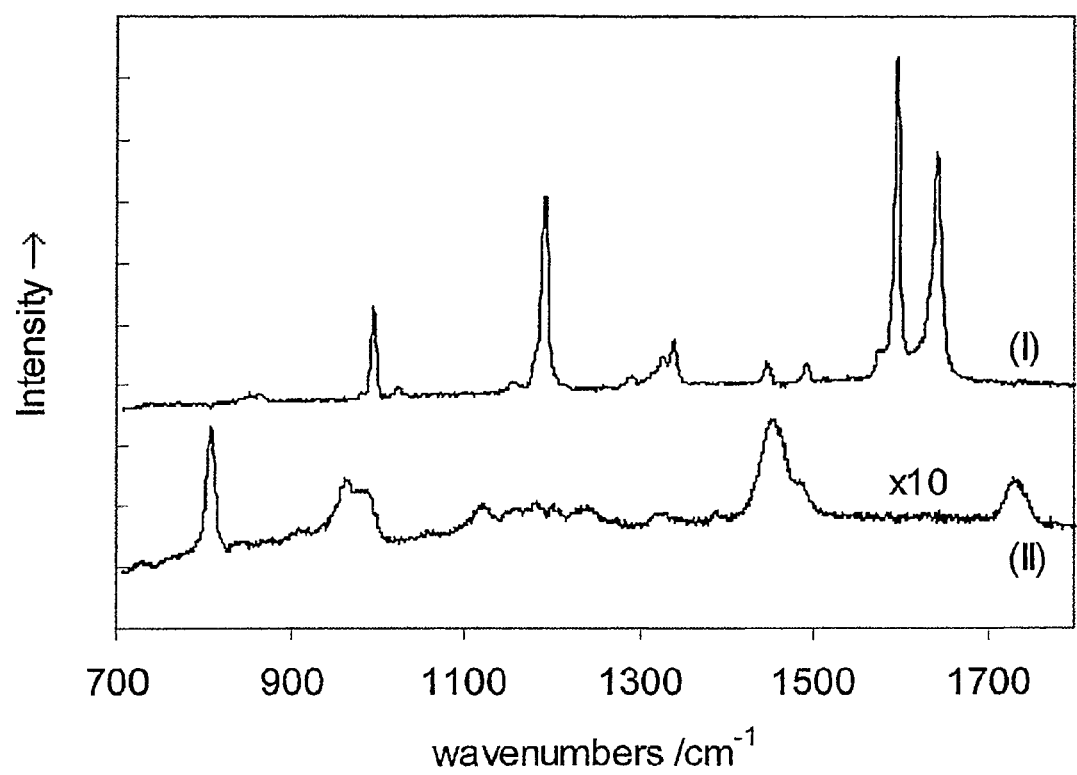
FIG. 18 shows the results of a simple subtraction process with respect to the same sample using Raman spectra obtained by the analysis method in accordance with the present invention.

In situations where a sample is known to consist of only two layers of different composition (if this is not known then this information can be obtained directly from pure PCA) the method and apparatus can be used to extract the pure signals of individual layers without the involvement of multivariate data analysis techniques. This is possible where the two spectra of the two layers each include an identifiable band or bands that do not overlap. In this situation a simple scaled subtraction can be used to separate the spectra of each of the individual layers from each other. In this process one Raman component is eliminated by a scaled subtraction of two spectra measured with two different spatial offsets cancelling out one or other spectral component in the process. The results of this simple extraction procedure are shown in FIG. 18. The spectra used in the analysis were measured with a zero and a 2 mm offset. The result is clearly satisfactory, although the applicability requires the above conditions to be satisfied. In contrast, the PCA analysis described above can be used in circumstances where there is no knowledge of the compositions of the different layers of a sample.

Thus, it will be apparent that it is not in all cases essential for a complete Raman spectrum to be generated with the present invention. Where there is some knowledge of the materials involved or the compositions to be detected, detection of individual Raman spectral features using, for example, one or more band pass filters is also encompassed by the SORS method and apparatus described herein.

The exact degree of the 'suppression' or separation of two layers in general situations depends on a variety of parameters. These parameters include the thickness of the top layer, that of the underlying matrix, the probe beam diameter, the exact collection geometry, the wavelength of the probe light used and the transport length of the medium. For non-invasive sub-surface probing, as a rule of thumb, it is believed that the ideal offset should be on the scale of the thickness or several thicknesses of the overlying medium. Also, for the technique to be effective the beam diameter should be smaller than the thickness of the top layer. In general terms the thinner the top layer is and the thicker the underlying matrix is favours a better spectral separation of the two components.

The use of probe light of particular wavelengths is not critical to this invention. The choice of probe wavelength is essentially a trade off between depth penetration, which improves with longer wavelength, and detector quantum efficiency, which is higher at shorter wavelengths. As mentioned earlier, the detector 3 used herein is a backilluminated deep depletion CCD detector based on silicon technology. This detector is selected as it has the best sensitivity and signal-to-noise ratio of those that are currently available, but alternatives can be used. Longer wavelengths avoid exciting $H_2O$ modes in Raman spectra, but the cut-off limit for Si detection is 1.1 μm. InGaAs detectors can be used at longer wavelengths, but these have currently reduced sensitivity.

With the method and apparatus of the present invention, substantially pure Raman spectra can be retrieved from depths well in excess of those accessible with conventional confocal microscopy. Moreover, the present invention has the advantage that it is compatible with the use of cw lasers beams and is suited to remote monitoring in both industrial and medical applications. Thus the method and apparatus are well suited to not only biomedical applications, where monitoring sub-surface tissue layers normally would require destroying surface tissue, but also many industrial analytical applications such as catalysts, food, and polymers research applications. The present invention may be used to detect contamination of food during manufacture or the deleterious breakdown of food in storage as well as the stability of stored pharmaceuticals in all cases without any contact with the sample.

We claim:

1. A method of measuring sub-surface Raman scattering through a diffusely scattering sample, comprising:
    (a) supplying incident radiation at one or more entry regions on a surface of the sample;
    (b) collecting light scattered within the sample, from a collection region on the surface, wherein one or more of the one or more entry regions is located around the collection region and at least one of the one or more entry regions is spaced from the collection region;
    (c) detecting, in the collected light, one or more Raman features spectrally related to the incident radiation; and
    (d) deriving, from the one or more Raman features, one or more characteristics of a sub-surface region of the sample,
    wherein incident radiation is supplied to a plurality of said entry regions each located at a different distance from said collection region, and the step of collecting comprises collecting light, separately for each entry region, at said collection region on the surface of the sample.

2. The method of claim 1, wherein at least one of the one or more entry regions located around the collection region forms an annulus around the collection region.

3. The method of claim 1, wherein said collection region is a central collection region surrounded by the one or more entry regions located around the collection region.

4. The method of claim 3, wherein the one or more entry regions located around the collection region are multiple annular entry regions having a range of radii.

5. The method of claim 4, wherein said multiple annular entry regions are broken or incomplete annular regions which surround said central collection region.

6. The method of claim 5, wherein a broken annulus includes multiple separate illumination regions distributed at similar distances from said central collection region.

7. The method as claimed in claim 5, wherein the incident radiation comprises two or more separate wavelengths and is generated by one or more lasers.

8. The method of claim 1, wherein the one or more entry regions located around the collection region includes a variable or fixed radius entry region located around said collection region.

9. The method of claim 1, wherein said collection region is a central collection region and at least one of the one or more entry regions located around the collection region is a broken or incomplete annular region including multiple separate illumination regions distributed at similar distances from said central collection region.

10. The method of claim 1, wherein the incident radiation is supplied by a plurality of optical fibres distributed around one or more collection optical fibres used to collect said light scattered within the sample.

11. The method of claim 1, wherein said collection region is a central collection region and the one or more entry regions located around the collection region include includes an annular illumination region surrounding said central collection region, thereby reducing a localised intensity of incident radiation required to generate a given number of Raman photons.

12. The method of claim 1, wherein step (c) comprises spectrally dispersing the collected light to form a Raman spectrum for each of said one or more entry regions.

13. The method of claim 1, wherein the step of detecting comprises detecting, separately for each different entry region, one or more Raman features spectrally related to the incident radiation.

14. The method of claim 13, wherein the step of deriving includes associating the Raman features associated with radiation from each of said entry regions with a different depth or distributions of depth within the sample.

15. The method of claim 13, further comprising combining the Raman features for the plurality of entry regions to preferentially select for a particular depth or range of depths.

16. The method as claimed in claim 13, wherein Raman features for at least two entry regions are collected and are analysed using a scaled subtraction, whereby Raman features for a sub-layer of the sample are identified.

17. The method as claimed in claim 13, wherein the Raman features for said plurality of entry regions are analyzed using multivariate data analysis.

18. The method of claim 1, wherein the step of collecting comprises collecting light from said collection region which is spaced by different distances from multiple entry regions.

19. The method of claim 1, wherein the one or more entry regions located around the collection region surrounds said collection region.

20. The method of claim 19, wherein each entry region located around the collection region is an annulus, and for each annulus, incident radiation is delivered to at least 10%, and more preferably at least 25% of the surface area of the annulus.

21. The method of claim 1, further comprising adjusting optics disposed in the path of the incident radiation to adjust the distance between the collection region and an entry region.

22. The method of claim 1, further comprising disposing one or more mirror elements adjacent to the sample surface outside the one or more entry regions to reflect light back into the sample.

23. The method as claimed in claim 1, wherein the Raman features for the chemical composition of the surface of the sample are known and the Raman features are analyzed by scaled subtraction of the known Raman features from the Raman features of the collected light.

24. The method as claimed in claim 1, wherein the plurality of Raman spectra are analysed using principal component analysis.

25. The method as claimed in claim 1, wherein the sample is irradiated at two or more different wavelengths and the collected light is a combination of Raman features and fluorescence and wherein the method comprises the further step of extracting the Raman features from the collected light.

26. The method as claimed in claim 1, wherein the collected light is spectrally dispersed using a spectrometer in combination with a CCD camera.

27. The method as claimed in claim 1, wherein the incident radiation is generated using a continuous wave laser.

28. The method as claimed in claim 1, wherein the incident radiation is at a wavelength of >200 nm and <2000 nm.

29. The method of claim 1, wherein one of said entry regions and said collection region are at the same place or substantially overlapping.

30. The method of claim 1, wherein said one or more entry regions and said collection region are non-overlapping.

31. Apparatus for measuring sub-surface Raman scattering through a diffusively scattering sample, comprising:

a light source arranged to supply incident radiation at one or more entry regions on a surface of the sample;

a collector arranged to collect light scattered within the sample, from a collection region on the surface, wherein one or more of the one or more entry regions is located around the collection region and at least one of the one or more entry regions is spaced from the collection region;

a detector arranged to detect, in the collected light, one or more Raman features spectrally related to the incident radiation; and an analyzer configured to derive, from the one or more Raman features, one or more characteristics of a sub-surface region of the sample, wherein incident radiation is supplied to a plurality of said entry regions each located at a different distance from said collection region, and the collector is arranged to collect light, separately for each entry region, at said collection region on the surface of the sample.

32. The apparatus of claim 31, wherein at least one of the one or more entry regions located around the collection region forms an annulus around the collection region.

33. The apparatus of claim 31, wherein said collection region is a central collection region surrounded by the one or more entry regions located around the collection region.

34. The apparatus of claim 33, wherein the one or more entry regions located around the collection region are multiple annular entry regions having a range of radii.

35. The apparatus of claim 33, wherein said multiple annular entry regions are broken or incomplete annular regions which surround said central collection region.

36. The apparatus of claim 31, wherein the one or more entry regions located around the collection region includes a variable or fixed radius entry region located around said collection region.

37. The apparatus of claim 31, wherein said collection region is a central collection region and at least one of the one or more entry regions located around the collection region is a broken or incomplete annular region including multiple separate illumination regions distributed at similar distances from said central collection region.

38. The apparatus of claim 31, wherein the incident radiation is supplied by a plurality of optical fibres distributed around one or more collection optical fibres used to collect said light scattered within the sample.

39. The apparatus of claim 31, wherein said collection region is a central collection region and the one or more entry regions located around the collection region includes an annular illumination region surrounding said central collection region, thereby reducing a localised intensity of incident radiation required to generate a given number of Raman photons.

40. The apparatus of claim 31, wherein the light source is arranged to supply incident radiation to the plurality of said entry regions each located a different distance from said collection region, and the collector is arranged to collect light, separately for each different entry region or distance, at said collection region.

41. The apparatus of claim 40, wherein the detector is arranged to detect, separately for each different entry region or distance, one or more Raman features spectrally related to the incident radiation.

42. The apparatus of claim 41, the analyzer being configured to combine the Raman features for the plurality of entry regions or distances, to preferentially select the features for a particular depth or range of depths.

43. The apparatus as claimed in claim 42, wherein the analyser is configured to perform a scaled subtraction between Raman features for at least two entry regions or distances.

44. The apparatus as claimed in claim 42, wherein the analyser is configured to perform multivariate data analysis on the Raman features for said plurality of entry regions or distances.

45. The apparatus as claimed in claim 42, wherein the analyser is configured to perform principal component analysis on the Raman features for said plurality of entry regions or distances.

46. The apparatus of claim 31, wherein the detector comprises a spectrometer arranged to spectrally disperse the collected light to separate out said Raman features associated with radiation irradiated at said one or more entry regions.

47. The apparatus of claim 31, wherein the detector comprises one or more filters arranged to selectively transmit said Raman features.

48. The apparatus of claim 31, wherein the one or more entry regions located around the collection region is provided by an annular region surrounding the collection region, said apparatus further comprising an optics arrangement configured to controllably adjust the diameter of the annular region.

49. The apparatus of claim 31, further comprising a masking device arranged to controllably adjust the spacing between said one or more entry regions and the collection region.

50. The apparatus of claim 31, further comprising one or more mirror elements disposed adjacent to the sample surface outside said one or more entry regions so as to reflect light back into the sample.

51. The apparatus as claimed in claim 31, wherein the light source comprises optical fibres arranged around the collector.

52. The apparatus as claimed in claim 31, wherein the optical fibres are arranged in a plurality of concentric circles around the collector.

53. The apparatus as claimed in claim 31, wherein the light source is a continuous wave laser.

54. The apparatus as claimed in claim 31, wherein the detector comprises a CCD camera.

55. The apparatus of claim 31, wherein one of said entry regions and said collection region are at the same place or substantially overlapping.

56. The apparatus of claim 31, wherein said one or more entry regions and said collection region are non-overlapping.

57. A method of detecting one or more sub-surface properties of a sample, comprising:
  directing probe light into said sample through one or more surface entry regions;
  collecting a portion of said probe light following scattering through said sample from said one or more entry regions to a surface collection region disposed within at least one of said one or more surface entry regions, wherein one of said one or more surface entry regions is offset from the collection region;
  detecting Raman spectral features in said collected probe light; and
  analyzing said Raman spectral features to derive said one or more sub-surface properties,
  wherein said probe light is supplied to a plurality of said entry regions each located at a different distance from said collection region, and the step of collecting comprises collecting light, separately for each entry region, at said collection region on the surface of the sample.

58. The method of claim 57,
  wherein the step of directing comprises directing probe light into said sample through a concentric plurality of said surface entry regions; and
  wherein the step of analyzing comprises combining the Raman spectral features for the plurality of surface entry regions to select for depth in said one or more sub-surface properties.

* * * * *